(12) United States Patent
Richards

(10) Patent No.: US 6,955,788 B2
(45) Date of Patent: Oct. 18, 2005

(54) APPARATUS AND METHOD FOR ALIGNING MICROARRAY PRINTING HEAD

(75) Inventor: John A. Richards, Middleton, MA (US)

(73) Assignee: Affymetrix, Inc., Santa Clara, CA (US)

(*) Notice: Subject to any disclaimer, the term of this patent is extended or adjusted under 35 U.S.C. 154(b) by 136 days.

(21) Appl. No.: 09/683,298

(22) Filed: Dec. 11, 2001

(65) Prior Publication Data

US 2003/0108868 A1 Jun. 12, 2003

Related U.S. Application Data

(60) Provisional application No. 60/318,094, filed on Sep. 7, 2001.

(51) Int. Cl.[7] ............................. G01N 21/00; C12M 1/36
(52) U.S. Cl. ..................... 422/56; 422/68.1; 422/100; 422/131; 435/283.1; 435/286.2; 435/286.4; 436/166; 436/180; 436/501
(58) Field of Search ..................... 422/56, 68.1, 100, 422/131; 436/166, 180, 501; 530/300, 333; 435/283.1, 286.2, 286.4

(56) References Cited

U.S. PATENT DOCUMENTS

| | | | | |
|---|---|---|---|---|
| 5,658,802 A | * | 8/1997 | Hayes et al. | 436/518 |
| 5,733,509 A | * | 3/1998 | Ackley et al. | 422/131 |
| 5,770,151 A | * | 6/1998 | Roach et al. | 422/63 |
| 5,807,522 A | * | 9/1998 | Brown et al. | 422/50 |
| 6,040,193 A | | 3/2000 | Winkler et al. | |
| 6,121,048 A | | 9/2000 | Zaffaroni et al. | |
| 6,136,269 A | | 10/2000 | Winkler et al. | |
| 6,269,846 B1 | | 8/2001 | Overbeck et al. | |
| 6,511,849 B1 | * | 1/2003 | Wang | 436/518 |

FOREIGN PATENT DOCUMENTS

| | | |
|---|---|---|
| WO | WO 200213967 A2 | 2/2002 |
| WO | WO 200213968 A2 | 2/2002 |
| WO | WO 200214531 A2 | 2/2002 |
| WO | WO 200214877 A2 | 2/2002 |

OTHER PUBLICATIONS

Webster's II New Riverside University Dictionary, 1994, Houghton Mifflin Comapny, pp. 126.*

* cited by examiner

*Primary Examiner*—Padmashri Ponnaluri
*Assistant Examiner*—My-Chau T. Tran
(74) *Attorney, Agent, or Firm*—William R. McCarthy, III; Philips L. McGarrigle; Alan B. Sherr

(57) ABSTRACT

An alignment apparatus and method are described for accurately and reliably depositing biological materials on a microscope slide or other substrate. A preferred implementation includes a first mounting assembly that enables rotation of deposit elements around a first axis perpendicular to the substrate surface using one or more bearing surfaces concentric with the first axis. A second mounting assembly enables rotation of the deposit elements around a second axis parallel to the depositing surface, and a third mounting assembly enables rotation of the deposit elements around a third axis that is parallel to the depositing surface and perpendicular to the second axis. Various types of deposit elements may be used, such as pins, quills, or jetting elements.

18 Claims, 9 Drawing Sheets

US 6,955,788 B2

APPARATUS AND METHOD FOR ALIGNING MICROARRAY PRINTING HEAD

CROSS REFERENCE TO RELATED APPLICATIONS

The present application claims priority from a U.S. Provisional Patent Application Ser. No. 60/318,094 entitled "Apparatus and Method for Providing Registered Microarray Printing Head," filed on Sep. 7, 2001, which is hereby incorporated by reference herein in its entirety for all purposes.

BACKGROUND OF INVENTION

1. Field of the Invention

The present invention relates to the deposit upon substrates of small quantities of fluid in arrays and, in particular, to devices and methods for depositing biological materials on substrates such as microscope slides.

2. Related Art

Mechanical deposition techniques have been used to make arrays of biological materials. Spotted arrays, such as those made using the Affymetrix® 417™ Arrayer, are simply one example of a mechanical deposition system. Arrays made with these devices are widely used to generate information about biological systems. Analysis of data from arrays may lead to the development of new drugs and new diagnostic tools. As the uses of spotted arrays has expanded, the demand has increased for devices and methods capable of making larger numbers of spotted arrays in a reasonable time and in a reliable and accurate manner.

SUMMARY OF INVENTION

Reference will now be made in detail to illustrative, non-limiting, embodiments. Various other alternatives, modifications and equivalents are possible. For example, while certain systems and methods may be described using illustrative embodiments with reference to the Affymetrix® 427™ Arrayer and spotted arrays made using that device, these systems and methods are not so limited. For example, they generally may be applied with respect to many other probe arrays and parallel biological assays and devices for making them. For example, the methods and devices are applicable to arrays made by other mechanical deposition methods such as those shown in U.S. Pat. No. 6,040,193, including the use of ink jetting, mechanical flow paths or other constraining means.

In accordance with one embodiment, an apparatus is described that includes elements that deposit biological materials on a depositing surface. A first mounting assembly enables movement of the deposit elements around a first axis perpendicular to the depositing surface; a second mounting assembly enables movement of the deposit elements around a second axis parallel to the depositing surface; and a third mounting assembly enables movement of the deposit elements around a third axis parallel to the depositing surface. In preferred implementations, the second and third axes are perpendicular to each other. Various types of deposit elements may be used, such as pins, quills, jetting elements, or any other element in accordance with known deposition technologies or those that may be developed in the future. In preferred implementations, the first mounting assembly is movable independently of one or both of the second and third mounting assemblies such that movement around the first axis is uncoupled from movement around one or both of the second and third axes, respectively. Also, the second mounting assembly may be movable independently of one or both of the first and third mounting assemblies such that movement around the second axis is uncoupled from movement around one or both of the first and third axes, respectively. The depositing surface may be a surface of a substrate. In some implementations, the apparatus includes a holding element that holds the substrate. For example, the holding element may be a platen upon which a substrate, such as a microscope slide, is placed. In such implementations, the depositing surface typically is substantially flat and the platen has a substantially flat surface that conformingly receives the bottom surface of the microscope slide, which also is substantially flat. In these contexts, the term "substantially flat" allows for waves, bumps, and various other irregularities such as, for example, would be observable upon microscopic or close inspection of the surfaces. The degree to which such irregularities are not acceptable in the substrate and/or platen depends on the required accuracy and reliability of the printing operation as will be appreciated by those of ordinary skill in the relevant art.

In some or all of these embodiments and implementations, the apparatus may also include one or more reference planes that may be used to register, i.e., align, the deposit elements. In one preferred implementation for registering in the yaw direction, for example, the reference plane may be an edge of a microscope slide, or a bar or other device parallel to the edge. With respect to registering the printing head in the pitch and roll directions, the reference plane may be the surface of the substrate, for example a microscope slide, or the platen. The apparatus may further include one or more elements that secures the deposit elements at a first position with respect to movement around the first axis, a second position with respect to movement around the second axis, and a third position with respect to movement around the third axis. For example, the securing elements may be lock bolts.

The first mounting assembly of these and other embodiments may have one or more bearing surfaces concentric with the first axis. For example, the first mounting assembly may comprise a print head mount that mounts the first mounting assembly to a gantry, and a head mounting plate that includes the one or more bearing surfaces. The head mounting plate is coupled to the deposit elements in these implementations. In these embodiments, the bearing surfaces provide references for the concentric movement of the deposit elements, and thus may be referred to in that context as reference surfaces for yaw adjustment. In these and other embodiments, the yaw adjustment may include rotating the depositing elements about the first axis without additional translation in a plane parallel to the depositing surface.

With respect to some embodiments, an apparatus is described that includes a first mounting assembly that enables movement of biological deposit elements around a first axis; a second mounting assembly that enables movement of the biological deposit elements around a second axis different from the first axis; and a third mounting assembly that enables movement of the biological deposit elements around a third axis different from the first and second axes. In accordance with other preferred embodiments, a method is described including enabling movement of biological deposit elements around a first axis perpendicular to a depositing surface; enabling movement of the biological deposit elements around a second axis parallel to the depositing surface; and enabling movement of the biological deposit elements around a third axis parallel to the depositing surface.

A system for generating spotted probe arrays is also described in accordance with other embodiments. The system includes an arrayer and a computer. The arrayer has a plurality of deposit elements that deposit biological materials on a depositing surface, a first mounting assembly that enables movement of the deposit elements around a first axis perpendicular to the depositing surface, a second mounting assembly that enables movement of the deposit elements around a second axis parallel to the depositing surface, and a third mounting assembly that enables movement of the deposit elements around a third axis parallel to the depositing surface. The computer includes a processor and a memory unit having stored therein a set of arrayer control instructions that, when executed in cooperation with the processor, controls one or more operations of the arrayer.

In further preferred embodiments, a method is described for registering a print head with respect to a surface. The method includes moving the print head in a yaw direction so that it is aligned with respect to a yaw reference; moving the print head in a roll direction so that it is aligned with respect to a roll reference; and moving the print head in a pitch direction so that it is aligned with respect to a pitch reference. The print head is constructed and arranged to deposit biological materials on the surface.

In accordance with yet other embodiments, an apparatus is described that includes a first mounting assembly coupled to deposit elements, constructed and arranged to rotate the deposit elements around a first axis perpendicular to the surface. The apparatus also includes a second mounting assembly coupled to the deposit elements constructed and arranged to rotate the deposit elements around a second axis parallel to the surface, and a third mounting assembly coupled to the deposit elements constructed and arranged to rotate the deposit elements around a third axis parallel to the surface and perpendicular to the second axis. In accordance with another embodiment, a method is described for registering deposit elements with respect to a surface of a substrate. The method includes the steps of: rotating the deposit elements around a first axis perpendicular to the surface; rotating the deposit elements around a second axis parallel to the surface; and rotating the deposit elements around a third axis parallel to the surface and perpendicular to the second axis.

A method is also described for fabricating an array of biological probes. The method includes providing a substrate having a surface to support the probes, providing deposit elements to deposit the probes on the surface, aligning the deposit elements around a first axis perpendicular to the surface and around second and third axes parallel to the surface, and depositing the probes on the surface after the deposit elements have been aligned. The probes may include oligonucleotides, polynucleotides, peptides, complex proteins, or any other type of biological material. The second and third axes may be perpendicular to each other. The deposit elements may include pins, quills, jetting elements, or any of a variety of other elements or devices for depositing materials.

The above embodiments are not necessarily inclusive or exclusive of each other and may be combined in any manner that is non-conflicting and otherwise possible, whether they be presented in association with a same, or a different, embodiment, aspect, or implementation. The description of one embodiment, aspect, or implementation is not intended to be limiting with respect to other embodiments, aspects, and/or implementations. Also, any one or more function, step, operation, or technique described elsewhere in this specification may, in alternative embodiments, aspects, or implementations, be combined with any one or more function, step, operation, or technique described in the summary. Thus, the above embodiments, aspects, and/or implementations are illustrative rather than limiting.

BRIEF DESCRIPTION OF DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 150 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION

Figure 1:
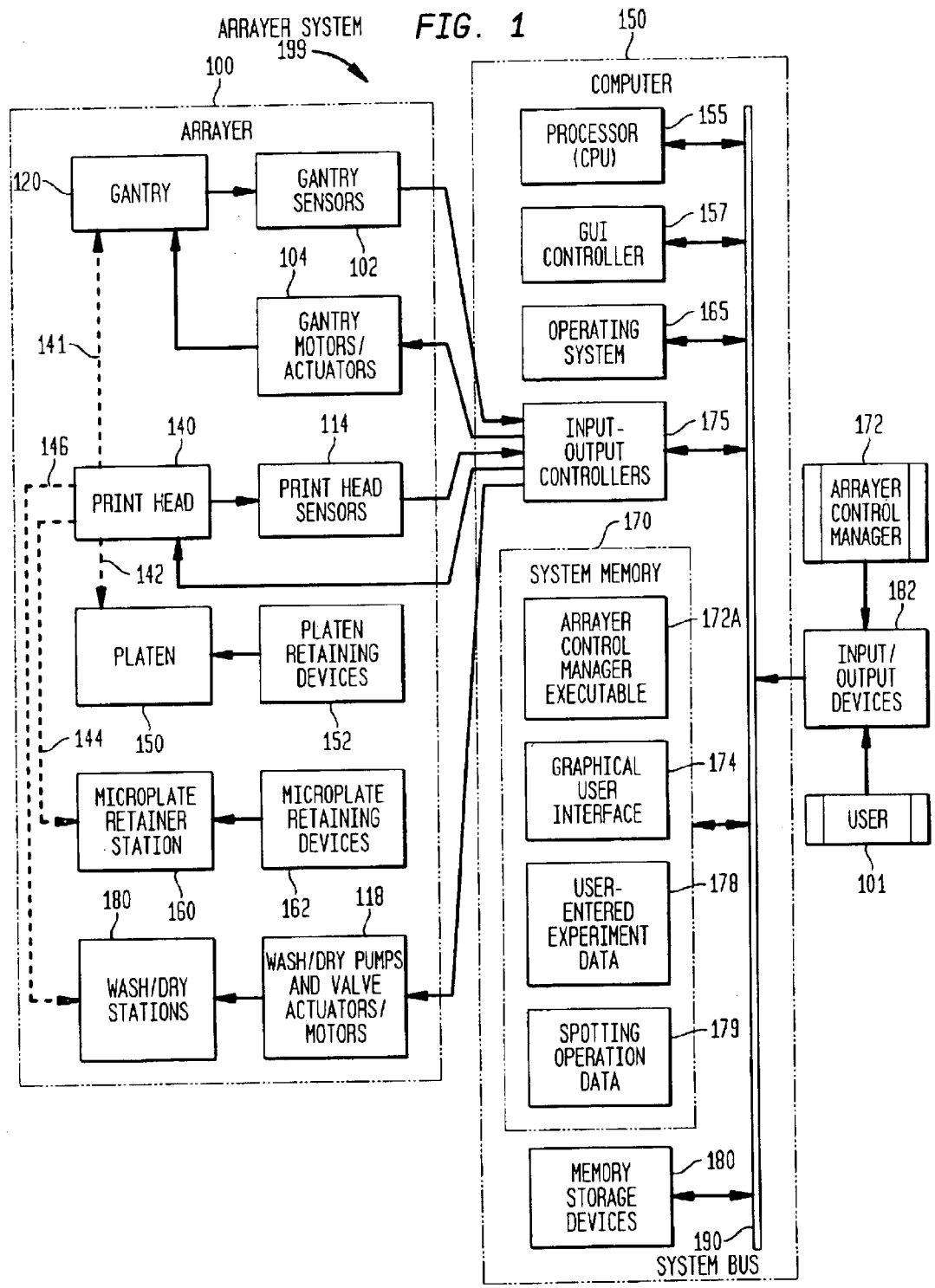
FIG. 1 is a functional block diagram of one embodiment of an arrayer system including an arrayer such as may include the print head illustrated in FIGS. 2–8, and a computer including software for controlling the arrayer and storing/processing arrayer spotting data.

As noted, techniques exist for depositing or positioning pre-synthesized or pre-selected probes on or within a substrate or support. For convenience, one type of array made by these techniques, or similar ones that may be developed in the future, is hereafter referred to as a spotted array. Typically, but not necessarily, spotted arrays are commercially fabricated on microscope slides. These arrays often consist of liquid spots containing biological material of potentially varying compositions and concentrations. For instance, a spot in the array may include a few strands of short polymers, such as oligonucleotides or peptides in a water solution, or it may include a high concentration of long strands of polymers, such as polynucleotides or complex proteins. The Affymetrix® 417™, 427™, and 437™ Arrayers are devices that deposit densely packed arrays of biological material on a microscope slide in accordance with these techniques. Aspects of these, and other, spot arrayers are described in U.S. Pat. Nos. 6,121,048, 6,040,193 and 6,136,269, in PCT Applications Nos. PCT/US99/00730 (International Publication Number WO99/36760) and PCT/US 01/04285, in U.S. patent application Ser. Nos. 09/122, 216, 09/501,099, and 09/862,177, and in U.S. Provisional Patent Application Ser. No. 60/288,403, all of which are hereby incorporated by reference in their entireties for all purposes. Other techniques for depositing or positioning biological probes on a substrate, i.e., creating spotted arrays, also exist. For example, U.S. Pat. No. 6,040,193 to Winkler, et al. is directed to processes for dispensing drops of biological material. The '193 patent, and U.S. Pat. No. 5,885,837 to Winkler, also describe separating reactive regions of a substrate from each other by inert regions and spotting on the reactive regions. The '193 and '837 patents are hereby incorporated by reference in their entireties. Yet other techniques for producing spotted arrays are based on ejecting jets of biological material. As noted in the '193 patent, some implementations of the jetting technique use devices such as syringes or piezo electric pumps to propel the biological material.

Spotted arrays typically are used in conjunction with tagged biological samples such as cells, proteins, polynucleotides, genes or EST's, other DNA sequences, or other biological elements. Other biological samples are noted in the '193 patent, incorporated by reference above. These samples, referred to herein as targets, typically are processed so that they are spatially associated with certain probes in the probe array. In one non-limiting implementation, for example, one or more chemically tagged biological samples, i.e., the targets, are distributed over the probe array. Some targets hybridize with probes and remain at the probe locations, while non-hybridized targets are washed away. These hybridized targets, with their tags or labels, are thus spatially associated with the probes with which they hybridized. The associated probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '832, '992, '138, and '092 patents, and publication WO99/05323, are incorporated by reference herein in their entirety for all purposes.

To ensure proper interpretation of the term probe as used herein, it is noted that contradictory conventions exist in the relevant literature. The word probe is used in some contexts in the literature to refer not to the biological material that is deposited on a substrate, as described above, but to what has been referred to herein as the target. To avoid confusion, the term probe is used herein to refer to compounds such as those deposited on a substrate to create spotted arrays, or oligonucleotides on synthesized arrays, as non-limiting examples.

Various aspects of a particular spotter implementation, referred to as arrayer 100 of arrayer system 199, are now described and may be illustrated in whole or part in relation to the Affymetrix® 427™ Arrayer. It is emphasized, however, that the features of the present invention are not limited to the 427 Arrayer, to illustrative arrayer 100, to arrayer system 199, to arrayers using pin and ring assemblies, to arrayers using pins or other depositing devices that may have channels or be hollow (as opposed to the solid pins of the 427 Arrayer implementation), and are not to be otherwise limited by the illustrated examples. Rather, the invention may be implemented in any other kind of device for making spotted arrays, such as jetting methods as non-limiting examples, and in other devices.

FIG. 1 is a functional block diagram of arrayer system 199 that includes arrayer 100 and computer 150. Computer 150, and software it executes to control arrayer 100, are described below. Principal components of preferred arrayer 100 include gantry 120, print head 140, platen 150, microplate retainer station 160, and wash/dry stations 180. Print head 140 includes various components described in detail with respect to FIGS. 2–8 such as, in one preferred embodiment, an Affymetrix® Pin-and-Ring™ assembly including the pins and rings, mounts for moving them, and related components, such as are commercially available from Affymetrix, Inc. with respect to the Affymetrix 417 and 427 Arrayers.

As noted, the 427 Arrayer automates the application of spots containing biological material onto a substrate, e.g., a microscope slide. The microscope slides (such as slide 206 shown in FIG. 2) are held on flat platen 150 that registers the sides relative to the printing head that is raised and lowered to effect the spotting of a sample onto the microscope slide. In one embodiment implemented in the 427 Arrayer, platen 150 accommodates 42 standard microscope slides in six columns and includes a horizontal aligning bar along the back of the slide area that contacts the back slide to keep the slides properly aligned. Vertical aligning bars may also be included to create separate columns of slides. Retaining springs may be used to force the slide against a vertical aligning bar. To place a slide on the platen, one simply retracts the retaining spring, places the slide on the platen and against the vertical aligning bar, and then releases the spring to secure the slide on the platen. If a second slide is added to a row, it is aligned by placing it adjacent to, and in contact with, the first slide. This procedure is repeated for slides two through seven in each row. A vertical aligning bar may be located to the right of each slide for contacting one edge of each slide, and one retaining spring may be located to the left of the slide to contact a second edge of each slide. The aligning bars and retaining springs are represented by platen retaining devices 152.

Platen 150 contains three recessed microplate holders that, in this illustrative implementation, accommodate three 96-well, or three 384-well microplates. A microplate (also commonly referred to as a "well plate" or a "microtiter plate") is placed in a corresponding recess referred to in this implementation as microplate retainer station 160, and is secured in place by pivoting tabs located on vertical bars, as represented by microplate retaining devices 162. Wash/dry stations 180, comprising two wash stations and one dry station in this example, are located in the front left corner of platen 150. The pin and ring assemblies of print head 140 are lowered into each wash station, which is flooded with wash fluid. The movement of print head 140 to stations 180 is represented by dashed line 146. Wash solution is provided from wash supply bottles located under the instrument. The pin and ring assemblies are then lowered into the dry station that utilizes a vacuum system supplied for example from a laboratory vacuum source such as a Venturi system or by an auxiliary vacuum pump, to suction off wash solution. The vacuum pump provides suction during a short period when a solenoid valve opens. These components supporting the wash and dry operations are represented by wash/dry pumps and valve actuators/motors 118.

During automated spotting in this illustrative implementation, print head 140 moves via gantry 120 over fixed platen 150 in a serpentine path from column to column. Gantry 120 of this implementation is a supporting mechanism that includes a screw drive on the X axis, i.e. from column to column. The gantry supports print head 140 and moves via a rail or other conventional arrangement, with the rail typically being fixed in relation to the body of the instrument. A rotational encoder counts turns of the screw to locate the gantry and thus the printing head along the X axis. A linear stepper is used to position the print head on the Y axis, i.e. along the length of a column. An open loop stepper motor counts steps to locate the print head along the Y axis. These components of gantry 120 are represented by gantry sensors 102 and gantry motors/actuators 104. In this implementation, gantry sensors 102 also sense limits of motion of gantry 120 to prevent damage.

Print head 140 is lowered and raised to effect the spotting of a sample onto each microscope slide. Arrayer 100 registers the position of the slide by its location relative to the home position of gantry 120, as indicated for example by gantry sensors 102. Several steps typically are performed during the spotting procedure. Initially, the pins and rings are cleaned at the wash station, and dried at the dry station. The print head then moves to the first microplate and dips the rings into the sample wells, and moves to the first slide, where the pins deposit a micro-drop of each sample to the slide. The print head then deposits a micro-drop of each sample at the same location on the second slide and on all specified subsequent slides in the slide group. Arrayer 100, under control of computer 150, may repeat these steps until all wells of the microplate have been addressed for the first microplate, as well as for second and third microplates, if present. Although three microplates may be retained in station 160 of this example, more than three microplates may be retained in other examples and/or arrayer 100 may pause after each group of three (or other number of) microplates, allowing the replacement of used microplates with fresh ones.

As described earlier, positioning gantry 120 moves print head 140 above platen 150. Print head 140 is secured to positioning gantry 120 via a ring mount in one preferred implementation. The ring mount, which stabilizes and holds the pins, is secured to a pin block, which is fixed to a yoke shaft by means of magnets. Dowels serve to secure pin and ring assemblies to the pin block. The coupling of print head 140 to gantry 120 is represented by line 141, which is dashed in FIG. 1 to indicate a physical relationship rather than information or control flow, as represented generally by the solid lines. As described in greater detail below with respect to FIGS. 2–8, the entire print head is capable of three directional movements: pitch, roll and yaw.

Pin-and-Ring™ assemblies such as used with the 427™ Arrayer can accommodate print heads designed for eight or 32 pins, although these numbers may of course be different in other implementations. The ring captures an aliquot of fluid from a microplate well of a microplate positioned in microplate retainer station 160, and the pins deposit a fraction of a fluid, such as a biological sample, onto a slide such as slide 206. The movement of print head 140 to station 160 is represented by dashed line 144. A plurality of pin and ring mechanisms included in the print head can be used to deposit many spots of biological samples in parallel, such as would be useful in preparing DNA microarrays. Specific aspects of pin and ring and other spotted arrayer technologies are described in greater detail in U.S. Pat. No. 6,269,846 to Overbeck, et al.; PCT Application No. PCT/US 01/04285 (International Publication No. WO 01/58593 A1); and U.S. patent applications, Ser. Nos. 09/501,099 (filed Feb. 9, 2000) and 09/862,177 (filed May 21, 2001), all of which are hereby incorporated by reference herein in their entireties for all purposes. Generally, the ring portion of the mechanism includes a circular ring section formed from a circular piece of metal. In a preferred implementation, the width or outer diameter of the ring is greater than its length. The ring is attached at the end of an arm section that extends from a cylinder. The top and bottom edges of the ring are uniform, except, of course, at the point of attachment of the top edge to the arm. The arm interconnects the ring and the cylinder section so that the opening in the ring aligns with the opening in the cylinder. The pin portion of the mechanism in this preferred implementation is a single, rod-like device having at one end a very narrow tip. The pin in this implementation is not hollow, but instead is fashioned from a solid piece of metal. During operation, the pin is inserted into and through the cylinder with the tip being capable of moving freely through the opening of the ring. The ring is not fixedly attached to the pin in this implementation. The pin and ring mechanism in a typical implementation measures approximately 1.5 inches when the cylinder and ring are inserted over the pin. The very bottom of the tip of the pin is designed to be flat and uniformly perpendicular to the sides of the pin, forming a ninety degree angle to the sides. The pin and ring in this implementation include male and female countersink portions for proper alignment of the pin through the ring opening during the spotting process.

The ring is lowered into a fluid sample contained, for example in a well of a microplate. The ring is entirely submerged in the fluid sample in this implementation. The pin is either kept stationery while the ring is lowered or the tip of the pin is positioned above the ring while both the pin and ring are lowered. The ring section is then raised out of the fluid sample. Given the design of the ring, an amount of the fluid sample is retained within the ring by the surface tension of the fluid and the surface activity of the inner wall of the ring. After the ring is raised out of the sample solution, the fluid held in the ring forms a convex meniscus that protrudes from the bottom opening of the ring. The ring with the sample can then be positioned at a location above a substrate onto which a fraction of the sample in the ring is to be deposited. The fluid volume in the ring is sufficient to deposit or spot more than one fraction. In fact, several hundred to a thousand or more fractions can be deposited from a single fluid sample retained in the ring. The number of fractions will depend on the desired volume of each fraction, the dimensions of the pin and the ring and the viscosity of the fluid sample.

Once the pin and ring mechanism is positioned over the desired location on the substrate, e.g., slide 206, the tip of the pin is then lowered into, through and out of the fluid sample retained in the ring. The surface tension of the fluid sample retains the fluid sample within the ring while the pin penetrates into and moves through and out of the fluid sample. A fraction of the fluid sample is retained on the tip of the pin forming a meniscus. The portion of the pin that passes through the ring has a diameter that is small compared to the diameter of the ring, enabling the pin to pierce the fluid sample without breaking the meniscus and causing the fluid sample to leave the ring. To provide proper registration, prevent damage, and monitor proper operation, print head sensors 114 monitor whether the pins and rings are in their home position during aspects of these operations.

The pin with the sample on the flat tip is lowered toward the surface of the substrate until the meniscus of the sample on the end of the pin makes initial contact with the surface of the substrate. During normal operation, the pin may contact the substrate without damaging force. The fluid sample then adheres via surface tension to the surface of the substrate, and as the pin is raised, the fluid sample is transferred to the surface of the substrate by surface tension and gravity. The pin is moved back through and above the fluid sample in the ring. The process of sample deposition can then be repeated by repositioning the print head at another desired location above the surface of the substrate. Alternatively, the print head can be positioned over another, different surface. Typically, the pin and ring mechanism does not dispense fluid samples into the wells of the well plates. Rather, the pin and ring mechanism removes fluid samples from the well plate wells and deposits them onto the surface of the glass slide. As noted, the 427 Arrayer of this illustrative implementation is designed to wash and dry the pins and rings in wash/dry stations 180 after each spotting effort to avoid contamination of fluid samples in the well plates and on the glass slides.

The pin and ring mechanism is engineered to retain a fluid sample within the ring and to deposit a uniform amount from the tip of the pin after it penetrates through the sample without breaking the sample meniscus. The precise engineering and delicate nature of the pin and ring mechanism generally provide that any contact with the substrate surface be minimized and be without any significant force that would alter the ability of the pin and ring mechanism to deliver a fluid sample with precision.

The ability of the pin and ring mechanism to deliver fluid sample with precision also generally depends on the proper registration of the print head with respect to the platen. As noted, the end of the pin is flat and forms a ninety degree angle to the sides of the pin. Provided that the assembly of pins approaches the platen at a ninety degree angle, the perimeter of the drops of fluids left by each pin will each generally approximate a circle, thus providing an approximately uniform volume of fluid in each radial direction from the center of the circle on the substrate. This uniformity may be an important factor in reliably and accurately reading emission signals from hybridized probe-target pairs, which may depend in part on volume. It therefore generally is desirable in some implementations that the print head be registered so that all eight or 32 pins (in the illustrative examples) approach platen 150 (and thus slide 206 or other substrate disposed on platen 150) at a ninety degree angle. More generally, in other implementations such as in jetting techniques or other techniques for depositing probes to make spotted arrays, the proper registration of the print head or printing components with the substrate typically also is important for ensuring consistent, uniform, and reliable spotting. That is, it generally is important that the print head or printing components be registered manually or automatically. For example, in a manual operation, a technician may adjust the print head in the three directional movements noted above: pitch, roll and yaw. Alternatively, control functions of a computer program executed on computer 150, as described below with respect to arrayer control manager executable 172A, may automatically register print head 140 by employing motors, actuators, sensors, and/or other components known to those or ordinary skill in the art to move print head 140 in the pitch, roll, and yaw directions. An illustrative design of the print head that enables these movements in a manual configuration is now described in greater detail with respect to FIGS. 2 through 8.

Figure 2:
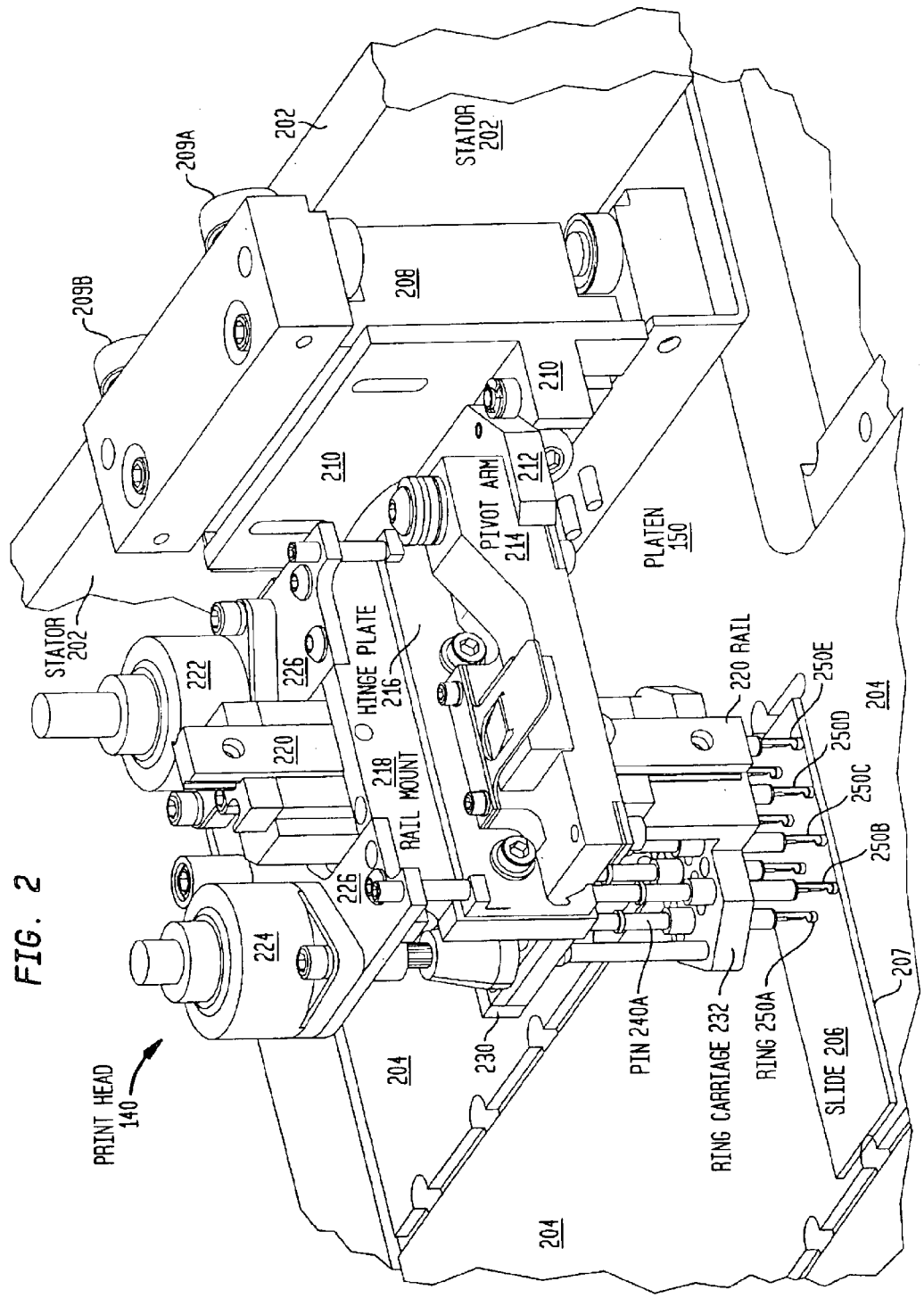
FIG. 2 is a perspective view of a print head mounted on a stator for movement over and in relation to a platen including one or more slides on which probes are disposed using the print head.

FIG. 2 is a perspective view of an illustrative print head 140 movably mounted on a stator 202 for movement over a platen 150. Stator 202 in this implementation is affixed to gantry 120. Slide 206 is secured to platen 150. In addition to print head 140, FIG. 2 shows stator 202 and linear motor assembly 208 that includes rollers 209A and 209B that are engaged with stator 202. Also shown in FIG. 2 is print head mount 210 that mounts print head 140 to linear motor assembly 208.

Component of print head 140 include head mounting plate 212 that engages with other components, such as locating rollers described below, that engage with print head mount 210. Additional components of print head 140, described in greater detail below, include pivot arm 214, hinge plate 216, rail mount 218, rail 220, ring motor 222, pin motor 224, pin and ring motor mount plate 226, pin carriage 230, ring carriage 232, pins 240 (such as the top of pin 240A shown in FIG. 2), and rings 250 (such as rings 250A–E of FIG. 2). Driven by motors 222 and 224, ring carriage 232 and pin carriage 230 slide in a vertical direction (sometimes referred to as the z direction) along rail 220. Rings 250 are held in ring carriage 232, and pins 240 are held in pin carriage 232. Pins 240 slide within rings 250 under the control of pin motor 224 so that, for example, the bottoms of pins 240 may be retracted up within rings 250 so as not to be visible in the configuration shown in FIG. 2. In some implementations, as shown in FIG. 2, it may be advantageous to register the bottoms of rings 250 with slide 206 or platen 150, and thus pins 240 are retracted in this illustration. For illustrative convenience, dashed line 142 represents the movement of print head 140 toward platen 150 for the purposes of depositing materials onto substrates disposed on the platen and/or for registering the print head against the platen or another surface to ensure printing integrity.

Figure 3:
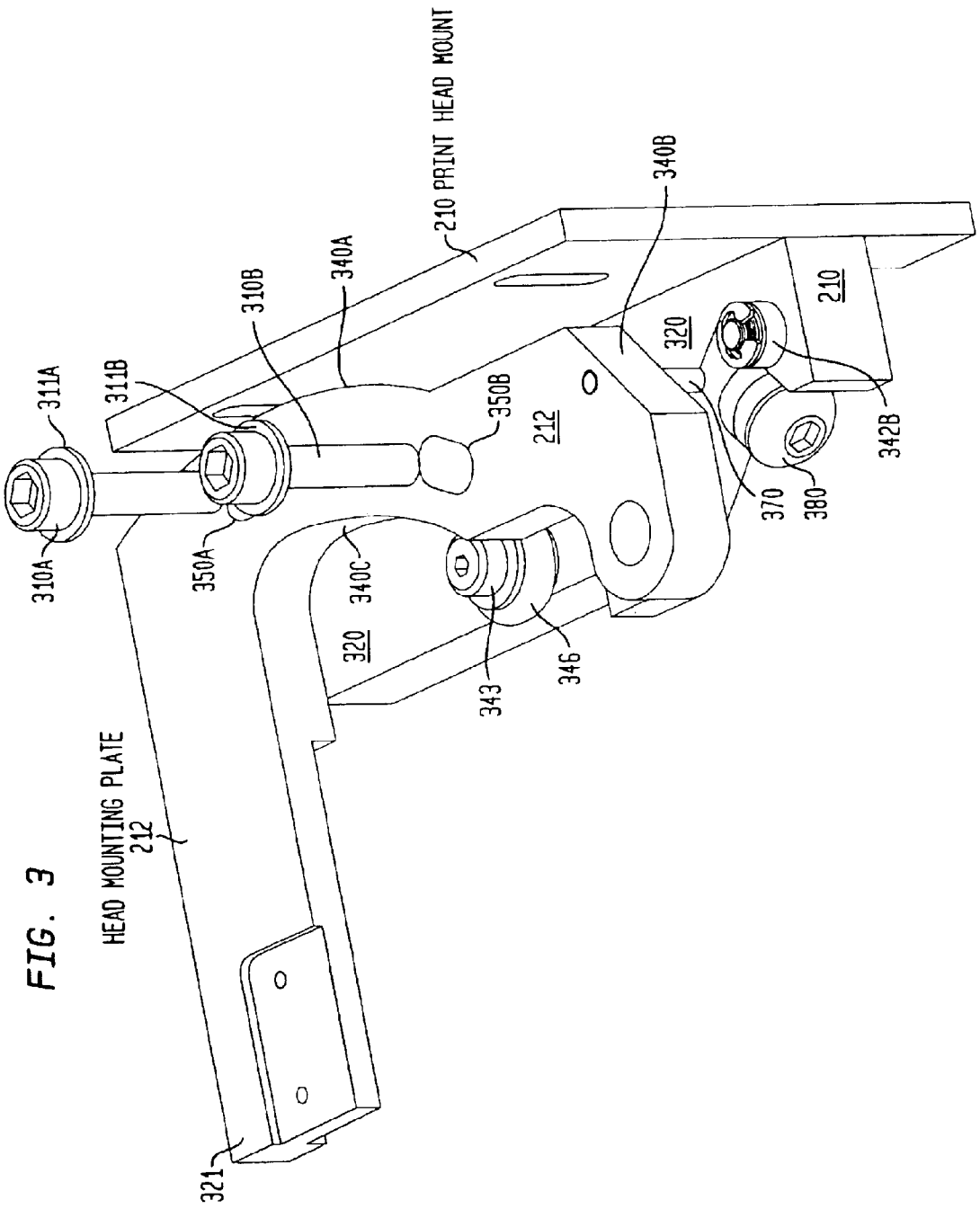
FIG. 3 is a perspective view of a portion of the print head of FIG. 2 showing in greater detail how the print head may be moved and registered in the yaw direction.
Figure 4:
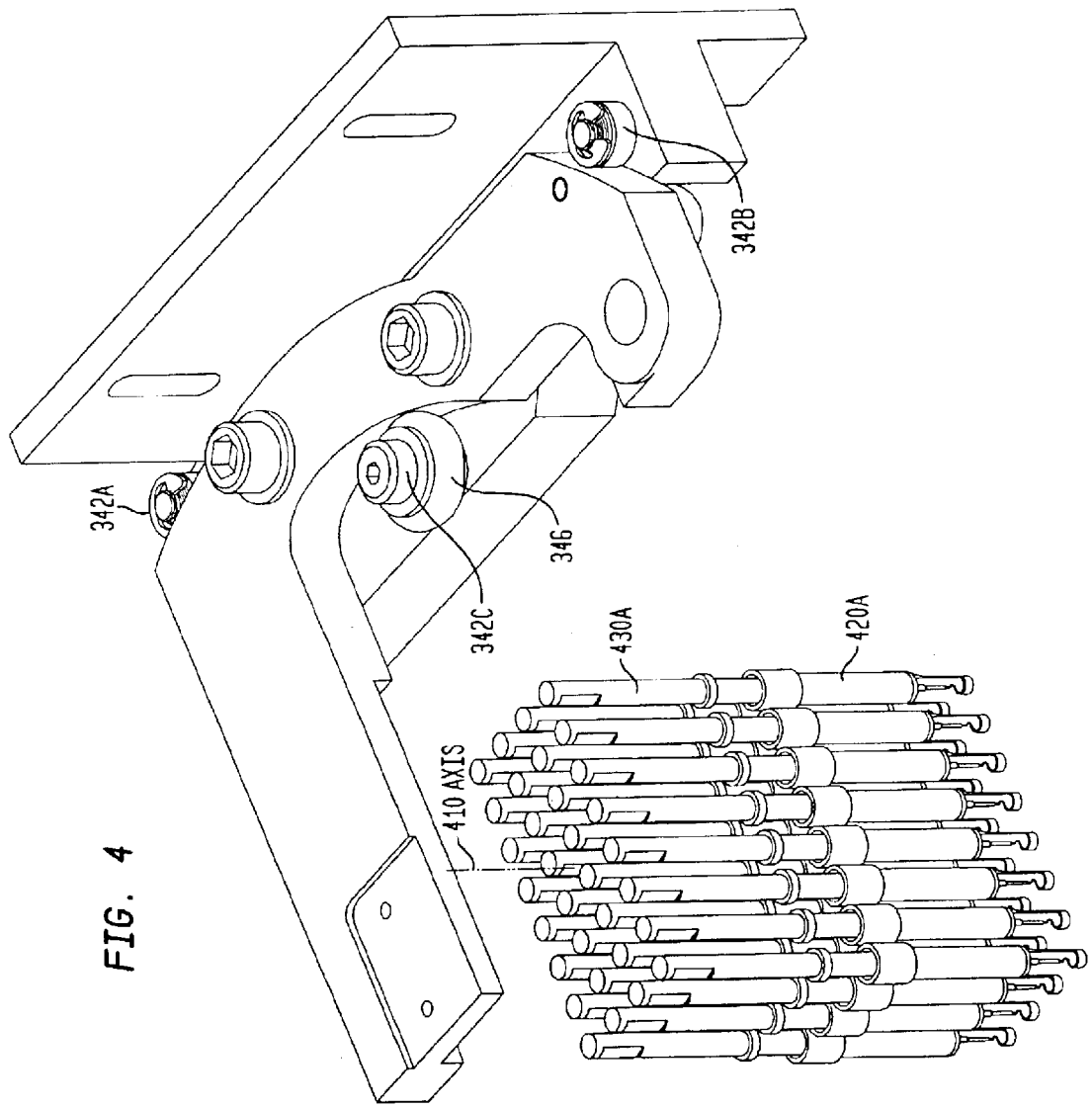
FIG. 4 is a second perspective view of the portion of the print head of FIG. 3 showing the print head disposed at a second position in the yaw direction and showing a projected central axis of surfaces concentric with a central axis of an array of deposit elements.

In accordance with one method of implementation, print head 140 may be registered against slide 206 by adjusting print head 140 in what will be referred to in the yaw direction. For example, print head 140 may be adjusted so that rings 250B–E align with edge 207 of slide 206. As shown in greater detail in FIGS. 3 and 4, this adjustment is made in the illustrated implementation by rotating head mounting plate 212 in a circular motion around an imagined central axis concentric with a central point of rings 250. The principal components of print head 140 of the present example that implement this circular motion are shown in FIG. 3. These components include head mounting plate 212 that is registered onto print head mount 210 by locking bolts 310A and 310B that include spring washers 311A and B, respectively. Bolts 310 may be loosened to release enough tension on washers 311 to allow plate 212 to slide on top surface 320 of print head mount 210 while bolts 310 are constrained within slots 350A and B, respectively. Plate 212 is further constrained by concentric bearing surfaces 340A, B, and C (generally and collectively referred to as surfaces 340), which are respectively in contact with locating bearings 342A and 342B (generally and collectively referred to as bearings 342) and with roller 343. (Bearing 340A is obscured in FIG. 3, but is seen in FIG. 4). Roller 343 includes a rotatable hub and a compliant rubber tire 346. Respective contact is maintained in this implementation between bearings 342 and surfaces 340 by pressure from roller 343 on surface 340C as exerted by tire 346. It will be understood that various other combinations of pressure exerting elements, restraining elements, and concentric surfaces may be employed in other implementations, and that the illustrated embodiment is just one of many approaches to implementing concentric yaw adjustment using two or more reference surfaces.

Adjusting pin 370 is, in this implementation, press fitted into mounting plate 212 and engages a circular groove (not shown) at the tip of adjusting bolt 380. A technician may turn bolt 380 in or out while locking bolts 310 are loosened, thus forcing mounting plate 212 to rotate about a central axis defined by concentric bearing surfaces 340. That is, surfaces 340 are fashioned so that they constitute arcs of concentric circles having a common central axis, shown in FIG. 4 as axis 410. Axis 410 is selected so that it is central to the depositing elements that, in this example, are the array of pins 430 and rings 420 (exemplified by pin 430A and ring 420A). Axis 410 is perpendicular to the substrate; i.e., axis 410 of this example is at a ninety degree angle with respect to the plane of the top surface of slide 206.

Since surfaces 340A and 340B are registered to rollers 342A and B, respectively, mounting plate 212 is constrained to rotate around central axis 410. Those of ordinary skill in the relevant arts will now readily appreciate how central axes and corresponding concentric surfaces may be selected for other arrays or combinations of depositing elements in other implementations. In these various implementations, the effect generally is to rotate the depositing elements about an axis perpendicular to the substrate without additional translation of the combination of elements in any direction.

Advantageously, the yaw direction adjustment just described generally is made independently of the roll and/or pitch adjustments described below. That is, the yaw registration generally need not be adjusted again to compensate for adjustments made in the roll and/or pitch directions. Moreover, all three adjustments, i.e., in the yaw, roll, and pitch directions, may be made independently of each other so that no adjustment typically need be repeated after one or more of the others are made. This independence of adjustments simplifies and speeds up the registration process while preserving the reliable and accurate registration of the deposit elements (in this example, the pins and rings) with the platen and slides.

Figure 5:
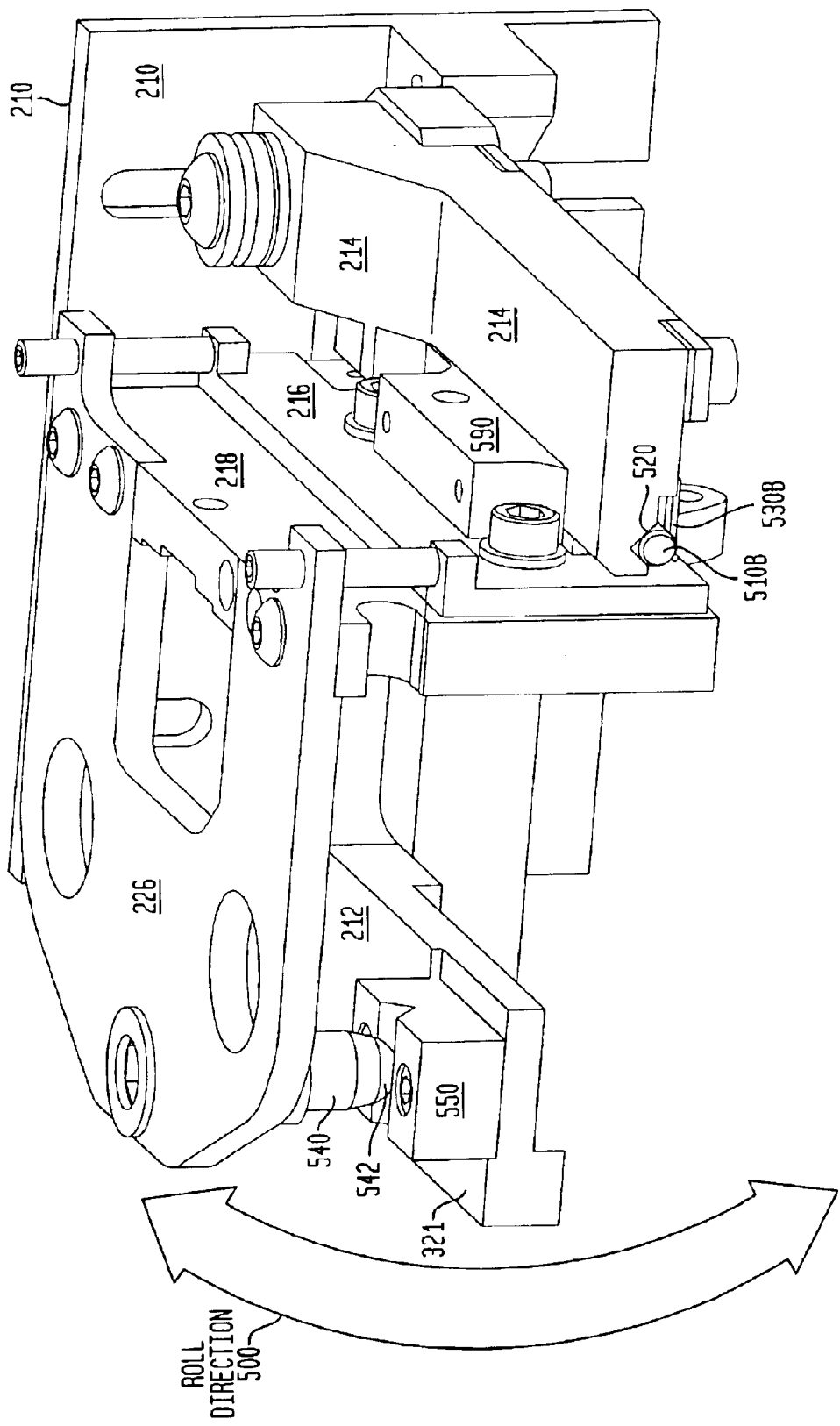
FIG. 5 is a perspective view of a portion of the print head of FIG. 2 showing in greater detail how the print head may be moved and registered in the roll direction.
Figure 6:
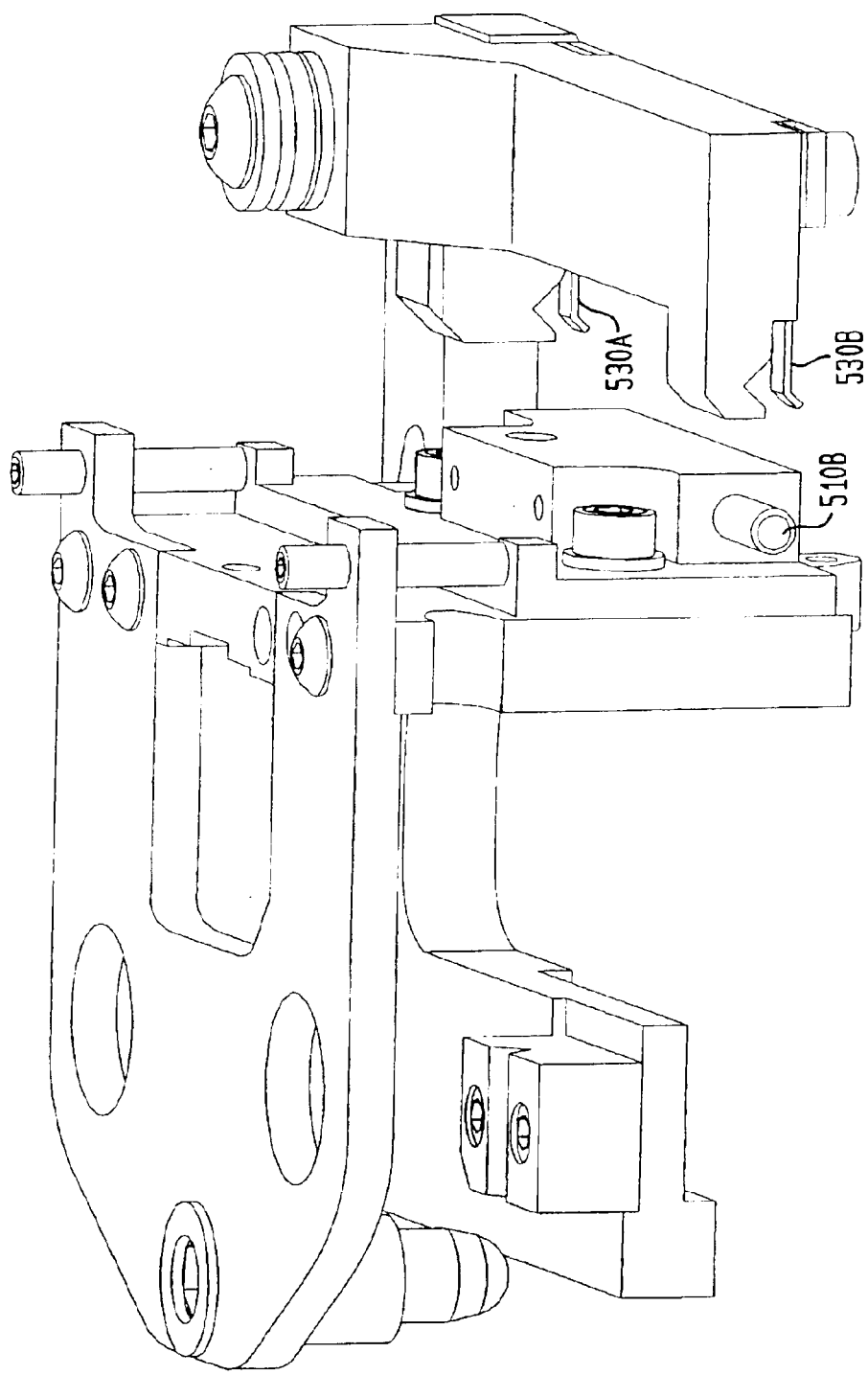
FIG. 6 is a second perspective view of the portion of the print head of FIG. 5 showing its components partially disengaged.

FIG. 5 is a perspective view of those components of print head 140 configured to move it in what will be referred to as the roll direction, indicated in FIG. 5 by roll direction arrow 500. In the illustrated implementation, coaxial pivot pins 510A and 510B define both the plane and axis of rotation of print head 140 in direction 500 when pivot pins 510 are registered in V groove 520 cut in pivot arm 214. (Pin 510A is not visible in FIGS. 5 and 6, but extends co-axially with pin 510B. In other implementations, a single pivot pin, or other hinge-like member, could be used.) Pivot pins 510 are registered into groove 520 by flat springs 530A and 530B (spring 530A is obscured in FIG. 5, but is visible in FIG. 6). It will now be appreciated by those of ordinary skill in the relevant art that there are many other techniques that could be employed to determine and provide the axis and plane of rotation and to register a pivot pin, hinge, or other member into the assembly. The degree of rotation, i.e., the tilt, of pin and ring motor mount plate 226 about the axis of pivot pins 510 is determined by the position of ball screw 540 that has a rotatable end 542. End 542 has a V shape conforming to a receiving V shape in reference member 550 that is attached, e.g., screwed, into plate 212. Thus, a technician may rotate screw 540 so as to shorten or lengthen its protrusion through plate 226 and thus cause plate 226 to rotate with relation to plate 212 about the axis defined by pivot pins 510. FIG. 6 is a perspective view similar to that of FIG. 5 except that pins 510 are disengaged from springs 530 to provide a clearer picture of how pins 510 are registered.

Figure 7:
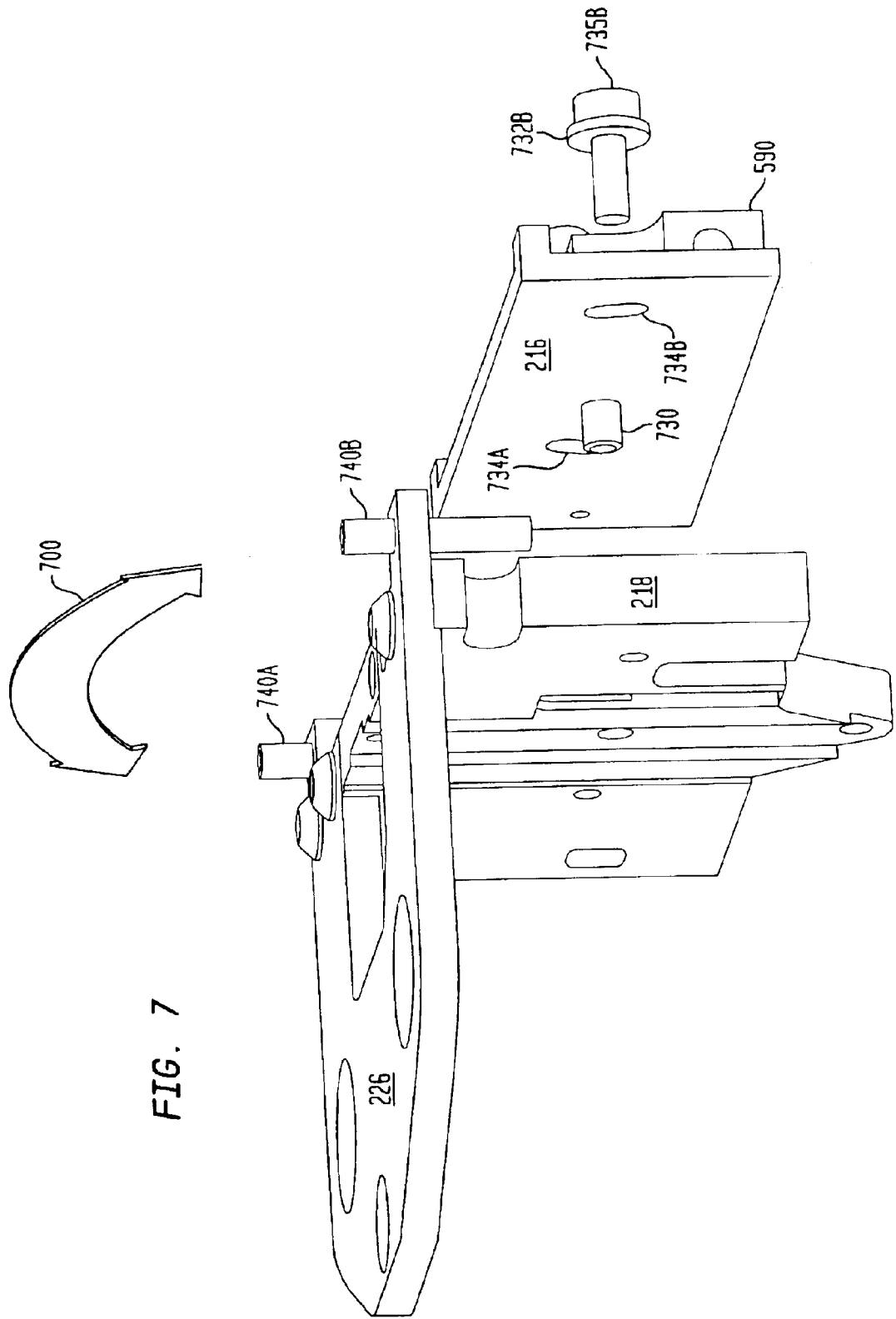
FIG. 7 is a perspective view of a portion of the print head of FIG. 2 showing in greater detail how the print head may be moved and registered in the pitch direction.
Figure 8:
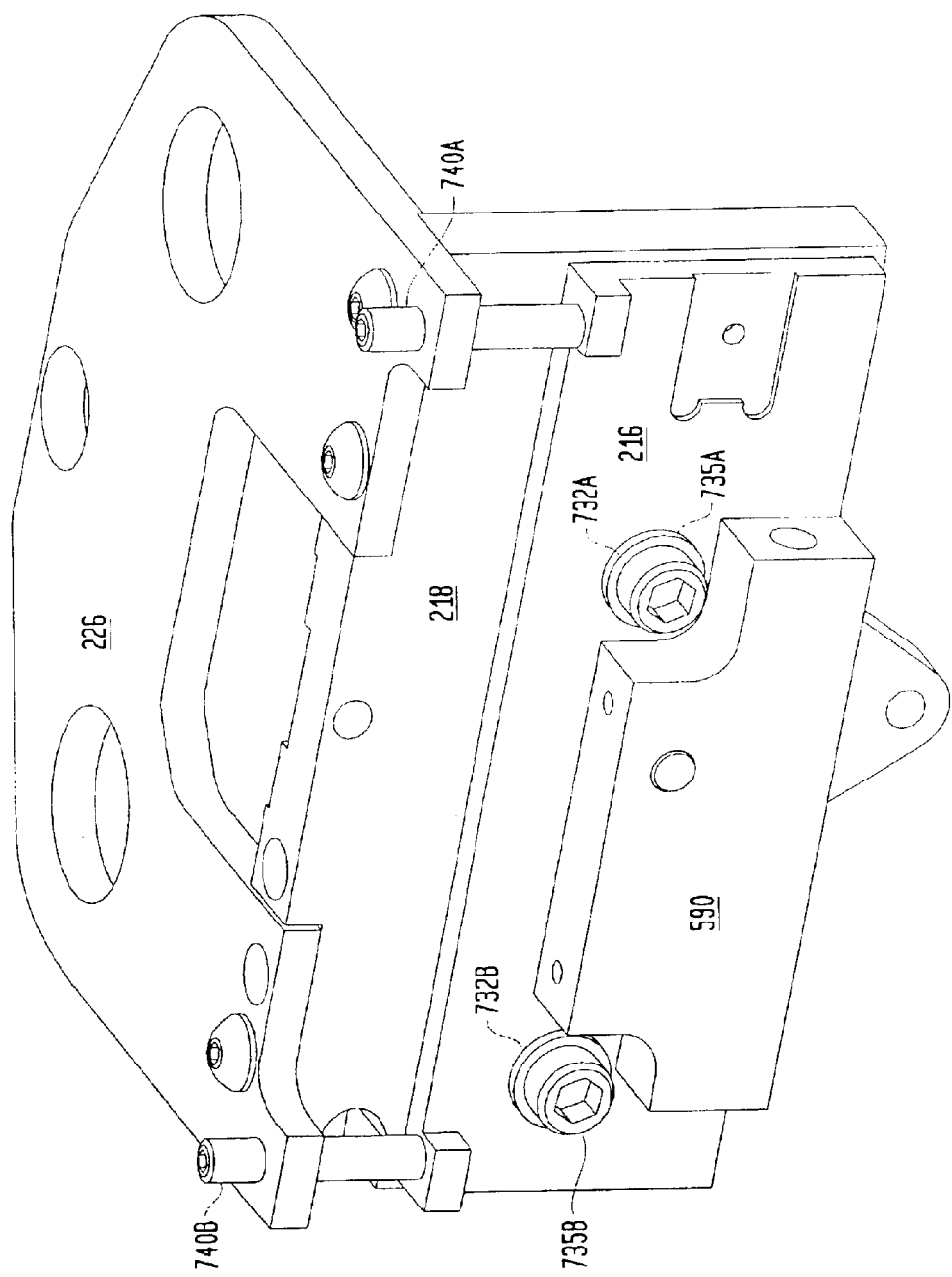
FIG. 8 is a second perspective view of the portion of the print head of FIG. 7.

FIG. 7 is a perspective view of those components of print head 140 configured to move it in what will be referred to as the pitch direction, indicated in FIG. 7 by pitch direction arrow 700. In the illustrated implementation, hinge plate 216 determines the pitch plane. Pivot dowel 730 in this implementation is press fitted into plate 216 and defines the rotation axis in the pitch direction. Locking screws 735A and 735B (735A is obscured in FIG. 7 but is visible in FIG. 8) are threaded into plate 218 through slotted holes 734A and 734B, respectively, that allow a determined degree of rotation of plate 216. Tightening or loosening of screws 735 fixes the relationship of plate 216 to plate 218. Spring washers 732A and 732B used in conjunction with locking screws 735A and B, respectively, allow screws 735 to be loosened sufficiently to allow relative motion between plates 216 and 218 while still providing enough force to maintain the registering surface of plate 216 in contact with the mating surface of plate 218. With locking screws 735 loosened slightly, adjusting screws 740A and 740B may be adjusted in a complimentary manner to force a controlled rotation of plate 218 relative to fixed (in this direction of movement) plate 216.

Returning now to FIG. 1, computer 150 may be a personal computer, a workstation, a server, or any other type of computing platform now available or that may be developed in the future. In the illustrated embodiment, computer 150 may be located locally to arrayer 100, or it may be coupled to arrayer 100 over a local-area, wide-area, or other network, including an intranet and/or the Internet. As shown in FIG. 1, computer 150 includes known components such as CPU 155, operating system 165, system memory 170, memory storage devices 180, graphical user interface (GUI) controller 157, and input-output controllers 175, all of which typically communicate in accordance with known techniques such as via system bus 190. GUI controller 157 may comprise any of a variety of known or future software programs for providing graphical input and output interfaces (e.g., graphical user interfaces 174 stored as instructions and/or data in memory 170) between computer 150 and a user 101 who wishes to use arrayer 100 to generate spotted arrays, and for processing inputs from user 101. GUI controller 157 is shown as functionally separate from memory 170 for convenience, but may be embodied as instructions stored in memory 170 in some implementations. System memory 170 may be any of a variety of known or future memory storage devices. Examples include any commonly available random access memory (RAM), magnetic medium such as a resident hard disk or tape, an optical medium such as a read and write compact disc, or other memory storage device. Memory storage devices 180 may be any of a variety of known or future devices, including a compact disk drive, a tape drive, a removable or internal hard disk drive, or a diskette drive. Such types of memory storage devices 180 typically read from, and/or write to, a program storage medium (not shown) such as, respectively, a compact disk, magnetic tape, removable or internal hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage medium used in conjunction with memory storage devices 180. A variety of other components may be included in computer 150, as is well known by those of ordinary skill in the relevant art.

In particular with respect to the illustrated implementation, arrayer control manager 172 is a software application or process that controls functions of arrayer 100 and processes data supplied by user 101 and generated by arrayer 100. As one non-limiting example, manager 172 may include the Affymetrix® 427™ Arrayer Control software and Plate Editor™ software. The 427 Arrayer Control software controls the 427 Arrayer and records the number and location of slides and microplates positioned in the Arrayer, the number of samples spotted from each microplate, and the number of replicate spots made on each slide. The Plate Editor software allows the production of lists containing contents and locations of wells in a microplate. Manager 172 may be written in any of a variety of high-level, or other, programming languages such as C++.

Various of these and other possible operations of illustrative and non-limiting embodiments of manager 172 are described in U.S. patent application Ser. Nos. 09/682,071, 09/682,074, and 09/682,076, and PCT Application No. PCT/US 01/26297, all of which are hereby incorporated herein by reference in their entireties for all purposes. As also described with respect to certain implementations in U.S. Provisional Patent Application Ser. No. 60/288,403, incorporated by reference above, manager 172, when executed in coordination with processor 155, operating system 165, and/or GUI controller 157, performs user interface functions, data processing operations, and data transfer and storage operations. For example, with respect to user interface functions, user 101 may employ one or more of GUI's 174 (displayed, for example, on a touch screen or other device of input/output devices 182) to specify and describe particular clones and their location in particular wells of particular microplates disposed in microplate retainer station 160. Using another of GUI's 174, the user may specify how spots of the clones are to be arranged in arrays on one or more slides such as slide 206. Yet another of GUI's 174 may be used to operate arrayer 100, e.g., to initiate the spotting of a number of slides without further user participation.

As will be evident to those skilled in the relevant art, manager 172 may be loaded into system memory 170 and/or memory storage devices 180 through an input device of input/output devices 182. Alternatively, manager 172 may be implemented as executable instructions stored in firmware. Executable code corresponding to manager 172 is referred to as arrayer control manager executable 172A and is shown for convenience with respect to the illustrated implementation as stored in system memory 170. However, instructions and data including executable instructions of application 170, and data used or generated by it, may be located in or shifted among other memory devices, local or remote, as convenient for data storage, data retrieval, and/or execution. Also stored in memory 170 in this illustrative implementation are user-entered experiment data, such as the name of user 101, the date of an experiment, and so on. Spotting operation data 179 may also be stored in memory 170 and include such information as probe identifiers; probe x and y coordinate identifiers; pin identifiers; and microplate or slide identifiers such as, for example, may be stored as a bar code or other machine-readable code on microplates and/or slides, see, e.g., U.S. Pat. No. 5,945,334, and European Patent Application No. EP 0799897, and read by an appropriate machine-reading device such as a bar-code scanner. The '334 patent and the '897 application are each hereby incorporated herein by reference in their entireties for all purposes. Executable 172A comprises a set of software instructions that cause arrayer control functions to be performed. Executable 172A may therefore be referred to as a set of arrayer control instructions.

Figure 9:
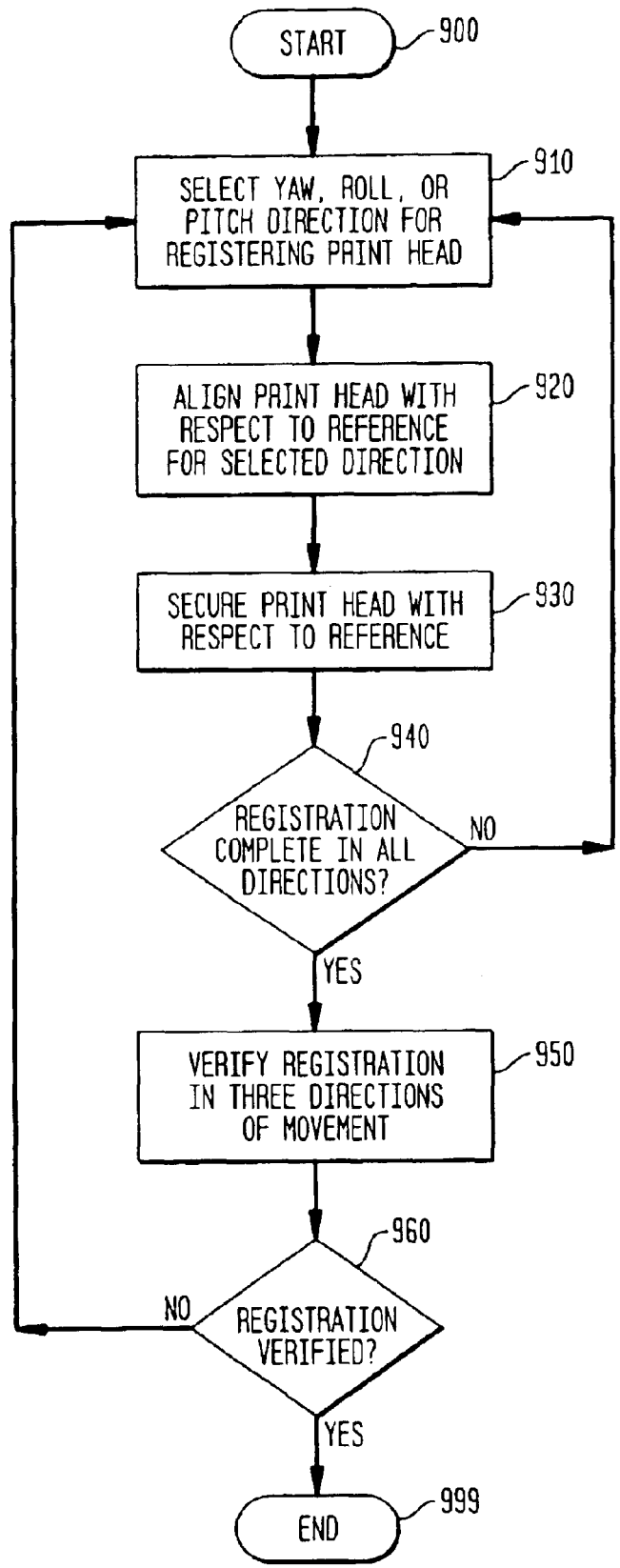
FIG. 9 is a flow chart showing one embodiment of a method for registering a print head, such as one employing the mechanisms shown in FIGS. 2–8.

FIG. 9 is a flow chart showing an illustrative method for registering a print head such as print head 140 described with respect to FIGS. 2–8. It will be understood, however, that this method is illustrative only and not limiting, and that various other methods can be employed in accordance with the present invention. As indicated in FIG. 9, the order of directions of movement in which the print head is registered may be varied because it is an advantage of various embodiments that registration in one direction is substantially independent of registration in another direction. Thus, for example, step 920 may include registering the bottoms of rings 250 with slide 206 or platen 150 if the roll or pitch direction of movement is selected in step 910. For instance, the bottoms of the rings may be disposed against, or otherwise aligned with, the slide or platen. If the yaw direction is selected in step 910, then step 920 may include aligning a row of rings 250 (e.g., rings 250B–E) with edge 207 of slide 206, or another reference in the yaw direction. Typically, step 930 of securing the print head is undertaken sequentially for each registration. For example, after print head 140 is registered in the yaw direction, lock bolts 310 may be tightened, then registration is done for one of the remaining directions of movement and it is secured, and similarly for the third direction of movement. Alternatively, registration in two, or all three, directions of movement may be done and then followed by a securing step in which all three directions are secured. Any other combination of alignment/registration and securing may be used in alternative implementations. An optional verification step 950 may be undertaken in which it is verified that, after locking bolts or other securing mechanisms have been engaged, print head 140 remains registered with respect to all references. As indicated by decision element 960, one or more of the registration steps may be repeated if registration is not verified.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Numerous other embodiments, and modifications thereof, are contemplated as falling within the scope of the present invention as defined by appended claims and equivalents thereto.

What is claimed is:

1. An apparatus, comprising:
  a plurality of deposit elements to deposit biological materials on a depositing surface;
  a first mounting assembly operatively coupled to the deposit elements, wherein the first mounting assembly comprises a first rotatable element that permits the deposit elements to rotate in a circular motion around a first axis perpendicular to the depositing surface;

a second mounting assembly operatively coupled to the deposit elements, wherein the second mounting assembly comprises a second rotatable element that permits the deposit elements to rotate in a circular motion in a roll direction around a second axis parallel to the depositing surface; and a third mounting assembly operatively coupled to the deposit elements, wherein the third mounting assembly comprises a third rotatable element that permits the deposit elements to rotate in a circular motion in a pitch direction around a third axis parallel to the depositing surface.

2. The apparatus of claim 1, wherein:

the deposit elements include pins, quills, or jetting elements.

3. The apparatus of claim 1, wherein:

the second and third axes are perpendicular to each other.

4. The apparatus of claim 1, wherein:

the first mounting assembly permits rotation independently of one or both of the second and third mounting assemblies such that the circular movement around the first axis is uncoupled from the circular movement around one or both of the second and third axes, respectively.

5. The apparatus of claim 1, wherein:

the second mounting assembly permits rotation independently of one or both of the first and third mounting assemblies such that the circular movement around the second axis is uncoupled from the circular movement around one or both of the first and third axes, respectively.

6. The apparatus of claim 1, wherein:

the depositing surface is a surface of a substrate; and the apparatus further comprises a holding element to hold the substrate.

7. The apparatus of claim 6, wherein:

the depositing surface is substantially flat.

8. The apparatus of claim 6, wherein:

the substrate includes a second substantially flat surface parallel and opposed to the depositing surface; and the holding element includes a platen having a substantially flat surface to conformingly receive the second surface of the substrate.

9. The apparatus of claim 8, wherein:

the substrate includes a microscope slide.

10. The apparatus of claim 1, further comprising:

one or more reference planes for registering the deposit elements.

11. The apparatus of claim 10, wherein:

the depositing surface includes a top surface of a microscope slide; and the one or more reference planes includes a yaw reference plane perpendicular to the first axis.

12. The apparatus of claim 1, further comprising:

one or more securing elements to secure the deposit elements at a first position with respect to circular movement around the first axis, a second position with respect to circular movement in the roll direction around the second axis, and a third position with respect to circular movement in the pitch direction around the third axis.

13. The apparatus of claim 12, wherein:

the first, second, and third positions are determined so that biological materials are deposited from each of the deposit elements at substantially a ninety degree angle to the depositing surface.

14. The apparatus of claim 1, wherein:

the first mounting assembly includes one or more bearing surfaces concentric with the first axis.

15. The apparatus of claim 14, further comprising:

a gantry; and wherein the first mounting assembly further includes a print head mount to mount the first mounting assembly to the gantry, and a head mounting plate coupled to the deposit elements and including the one or more bearing surfaces.

16. The apparatus of claim 1, wherein:

the first mounting assembly provides yaw adjustment using two or more reference surfaces.

17. The apparatus of claim 16, wherein:

the yaw adjustment includes rotating the depositing elements about the first axis without additional translation in a plane parallel to the depositing surface.

18. An apparatus, comprising:

a first mounting assembly operatively coupled to a plurality of biological deposit elements, wherein the first mounting assembly comprises a first rotatable element that permits the deposit element to rotate in a circular motion around a first axis;

a second mounting assembly operatively coupled to the biological deposit elements, wherein the second mounting assembly comprises a second rotatable element that permits the deposit elements to rotate in a circular motion in a roll direction around a second axis different from the first axis; and a third mounting assembly operatively coupled to the biological deposit elements, wherein the third mounting assembly comprises a third rotatable element that permits the deposit elements to rotate in a circular motion in a pitch direction around a third axis different from the first and second axes.

* * * * *